United States Patent
Uhr et al.

(10) Patent No.: US 8,030,033 B2
(45) Date of Patent: Oct. 4, 2011

(54) POLYMORPHISMS IN ABCB1 ASSOCIATED WITH A LACK OF CLINICAL RESPONSE TO MEDICAMENTS

(75) Inventors: Manfred Uhr, Stockdorf (DE); Florian Holsboer, Munich (DE); Elisabeth Binder, Munich (DE); Bertram Mueller-Myhsok, Munich (DE)

(73) Assignee: Max-Planck-Gesellschaft zur Forderung der Wissenshaften e.V., Munich (DE)

( * ) Notice: Subject to any disclaimer, the term of this patent is extended or adjusted under 35 U.S.C. 154(b) by 474 days.

(21) Appl. No.: 11/596,177

(22) PCT Filed: May 12, 2005

(86) PCT No.: PCT/EP2005/005194
§ 371 (c)(1),
(2), (4) Date: Dec. 12, 2006

(87) PCT Pub. No.: WO2005/108605
PCT Pub. Date: Nov. 17, 2005

(65) Prior Publication Data
US 2008/0064609 A1    Mar. 13, 2008

Related U.S. Application Data

(60) Provisional application No. 60/570,085, filed on May 12, 2004.

(51) Int. Cl.
*C12P 19/34* (2006.01)
(52) U.S. Cl. .................................................. 435/91.2
(58) Field of Classification Search .................. 435/91.2
See application file for complete search history.

(56) References Cited

U.S. PATENT DOCUMENTS

2003/0073713 A1    4/2003    Schoenhard
2005/0069936 A1*   3/2005    Diamond et al. .................. 435/6

FOREIGN PATENT DOCUMENTS

WO    WO 01/09183 A    2/2001

OTHER PUBLICATIONS

Siddiqui et al., "Association of multidrug resistance in epilepsy with a po9lymorphism in the drug-transporter gene ABCB1," The New England Journal of Medicine, Apr. 10, 2003, vol. 348, No. 15, pp. 1442-1448.*
Uhr et al. Biol. Psychiatry, col. 54, pp. 840-846, 2003.*
Lakham et al. Epilepsy and Behavior, vol. 14, pp. 78-82, 2009.*
Lucentini. The Scientitist, vol. 20, p. 16, Dec. 2004.*
Uhr et al. Neuron, vol. 57, pp. 203-209, Jan. 2008.*
Marzolini et al., "Polymorphism in human MDR1 (P-glycoprotein): Recent advances and clinical relevance", Clinical Pharmacology & Therapeutics, vol. 75, No. 1, Jan. 2004, pp. 13-33.
Database SNP, Online! 2001, XP002347791, retrieved from NCBI, Database accession No. ss3189005 abstract.
Roberts et al., "A common P-glycoprotein polymorphism is associated with nortriptyline-induced postural hypotension in patents treated for major depression", Pharmacogenomics Journal, vol. 2, No. 3, 2002, pp. 191-196.
Kerb et al., "ABC Drug Transporters: Hereditary Polymorphisms and Pharmacological Impact in MDR1, MRP1 and MRP2", Pharmacogenomics, vol. 2, No. 1, Feb. 2001, pp. 51-64.
Ackenheil et al., "Differing response to antipsychotic therapy in schizophrenia: Pharmacogenomic aspects", Dialogues in Clinical Neuroscience 2004, vol. 6, No. 1, 2004, pp. 71-77.
Zimprich et al., "Association of an ABCB1 gene haplotype with pharmacoresistance in temporal lobe epilepsy", Neurology, Sep. 28, 2004, vol. 63, No. 6, Sep. 28, 2004, pp. 1087-1089.

* cited by examiner

*Primary Examiner* — Gary Benzion
*Assistant Examiner* — Cynthia Wilder
(74) *Attorney, Agent, or Firm* — Rothwell, Figg, Ernst & Manbeck, P.C.

(57) ABSTRACT

The present invention relates to methods, compositions and kits for determining the prognosis of a clinical response in a human patient to a medicament which acts in the central nervous system and which is a substrate of the ABCB1 protein. Further, the invention relates to a combination of medicaments for the treatment of human patients having specific polymorphisms in the ABCB1 gene.

16 Claims, 4 Drawing Sheets

Figure 1:
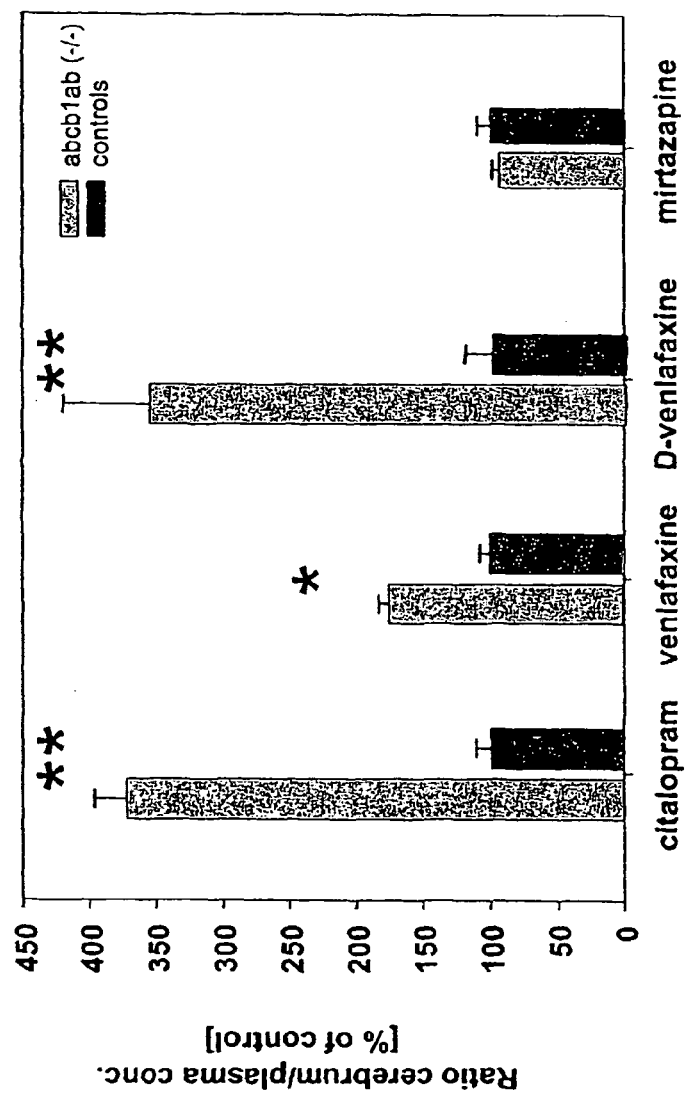

POLYMORPHISMS IN ABCB1 ASSOCIATED WITH A LACK OF CLINICAL RESPONSE TO MEDICAMENTS

CROSS REFERENCE TO RELATED APPLICATION

This application is a 35 USC §371 National Phase Entry Application from PCT/EP2005/005194, filed May 12, 2005, and designating the United States which claims the benefit of U.S. Provisional 60/570,085, filed May 12, 2004.

DESCRIPTION

The present invention relates to methods, compositions and kits, and reagents for determining the prognosis of a clinical response in a human patient to a medicament which acts in the central nervous system (CNS) and which is a substrate of the ABCB1 protein. Further, the invention relates to a combination of medicaments for the treatment of human patients having specific polymorphisms in the ABCB1 gene.

Depression is a very common medical disorder, with lifetime prevalences of up to 14%, thus affecting millions worldwide. While antidepressants are the most effective treatment for depressive disorders, there still is substantial need for improvement of therapy. So far there are no objective criteria for the choice of the optimal antidepressant treatment for an individual patient. Depressed patients are therefore treated on a trial and error basis, resulting in a failure rate of a single treatment attempt in up to 30-40%, even in the presence of sufficiently high plasma levels[1]. Sufficient plasma drug levels considered to elicit a clinical response may, however, not translate into adequate intracerebral drug levels in all patients because of activities of transporter molecules expressed at the luminal membrane of the endothelial cells lining the small blood capillaries which form the blood-brain barrier. One of the most studied molecules of this the latter class is p-glycoprotein[2,3]. P-glycoprotein is a member of the highly conserved superfamily of ATP-binding cassette (ABC) transporter proteins[4]. In humans, this 170-kDa glycoprotein is encoded on chromosome 7 by the ABCB1 gene, also known as the multidrug resistance 1 (MDR1) gene[5,6]. This plasma membrane protein actively transports its substrates against a concentration gradient. P-glycoprotein acts as an active efflux pump for xenobiotics as well as for endogenous substrates such as some steroids[7,8].

It was found that the ABCB1 protein is involved in the uptake of citalopram and trimipramine into the brain of mice. It was speculated that inter-individual differences in the activity of the ABCB1 gene can account in part for the great variation in clinical response to antidepressants in psychiatric patients, even at comparable plasma levels[26]. There is, however, no suggestion that there are polymorphisms in the ABCB1 gene which are associated with a lack of clinical response to medicaments. A further study showed different enhancement of penetration of the antidepressants doxepin, venlafaxine and paroxetine in the brain of mice with an abcb1ab knockout mutation[29]. Polymorphisms in the ABCB1 gene associated with a clinical response to medicaments are, however, not disclosed.

An investigation of polymorphisms in the ABCB1 gene and antidepressant-induced mania showed that there was no association between antidepressant-induced mania and ABCB1 alleles or genotypes[30]. These results seem to indicate that polymorphisms in the ABCB1 gene are not of clinical significance. Further, a recent review article indicates that previously reported effects of polymorphisms in the ABCB1 gene have been inconsistent and in some cases conflicting[31].

WO 01/09183 discloses polymorphisms in the human ABCB1 gene for the use in diagnostic tests to improve therapy of established drugs and help to correlate genotypes with drug activity and side effects. This document does not disclose polymorphisms associated with the clinical response to antidepressants. US 2001/0034023 generally relates to methods for identifying sequence variations in different genes to assess efficacy and safety of medical therapies. Although, SNPs in the ABCB1 gene are mentioned, there is no evidence for specific polymorphisms associated with the clinical response to antidepressants.

Thus, until now, no polymorphisms in the ABCB1 gene have been identified which have a clear and significant association with the clinical response to medicaments which act in the central nervous system and which are substrates of the ABCB1 protein.

In this study it was tested whether three commonly used antidepressants are substrates of p-glycoprotein, using transgenic mice lacking the homologues of ABCB1 and their wild-type littermates. Then the association of single nucleotide polymorphisms (SNPs) in the ABCB1 gene with clinical response to antidepressant drugs was investigated in 255 depressed patients.

Surprisingly, polymorphisms in the ABCB1 gene, particularly located in the introns of the genes, were identified which have a clear and statistically relevant association with an insufficient clinical response, e.g. a remission status of the six weeks of treatments with the antidepressants citalopram, paroxetine and/or venlafaxine. Genotyping of these polymorphisms allows to predict the clinical response to a substrate of ABCB1 with a certainty of over 75%, opening up a route towards genotype-based diagnostic and therapeutic methods.

A first aspect of the invention relates to a method for determining the prognosis of a clinical response in a human patient to a central nervous system (CNS)-active medicament which is a substrate of the ABCB1 protein wherein the presence of at least one polymorphism in the ABCB1 gene of said patient is determined wherein said polymorphism is associated with a delayed, partial sub-optimal or lacking clinical response to said medicament.

A further aspect of the invention relates to a diagnostic composition or kit for the prognosis of a clinical response in a human patient to a CNS-active medicament which is a substrate of the ABCB1 protein comprising at least one prime or probe for determining at least one polymorphism in the ABCB1 gene in said patient wherein said polymorphism is associated with a delayed, partial sub-optimal or lacking clinical response to said medicament.

Still a further aspect of the invention relates to a microarray for the prognosis of a clinical response in a human patient to a CNS-active medicament which is a substrate of the ABCB1 protein comprising a carrier having immobilized thereto at least one probe for determining at least one polymorphism in the ABCB1 gene in said patient wherein said polymorphism is associated with a delayed, partial sub-optimal or lacking clinical response to said medicament:

Still a further aspect of the invention relates to a prime or probe for the prognosis of a clinical response in a human patient to a CNS-active medicament which is a substrate of the ABCB1 protein comprising a carrier having immobilized thereto at least one probe for determining at least one polymorphism in the ABCB1 gene in said patient wherein said polymorphism is associated with a delayed, partial sub-optimal or lacking clinical response to said medicament.

Finally, a further aspect of the invention relates to a therapeutic composition or kit comprising:
(a) a CNS-active medicament which is a substrate of the ABCB1 protein;
(b) a further medicament which is an inhibitor of the ABCB1 protein for treating a human patient having: at least one polymorphism in the ABCB1 gene wherein said polymorphism is associated with a delayed, partial, sub-optimal or lacking clinical response to said medicament (a).

The present invention discloses for the first time polymorphisms in the human ABCB1 gene which have a statistically significant association with a delayed, partial sub-optimal or lacking clinical response to medicaments which act in the central nervous system and which are substrates of the ABCB1 protein. A statistically significant association is preferably p<0.05, more preferably p<0.01 and most preferably p<0.001. The polymorphisms are preferably single nucleotide polymorphisms (SNPs). Surprisingly, it was found that polymorphisms associated with a delayed, partial sub-optimal or lacking clinical response to a medicament may occur in exons, introns and/or the 3'UTR sequence of the human ABCB1 gene, e.g. in exon 29, intron 5, 13, 21, 22 or 23 and/or the 3'UTR sequence of the human ABCB1 gene.

Preferably, the polymorphisms are selected from the group consisting of rs 2235015, rs 2235040, rs 2235067, rs 2032583, rs 17064, rs 2032588, rs 1055302 and combinations thereof. More preferably, the polymorphism is 2235015 or rs 2235040. Most preferably, the polymorphism is rs 2235015. The sequence of the human ABCB1 gene including the introns is described in the human reference sequence of the National Center for Biotechnolgy Information (NCBI). The sequence is accessible gene databases such of NCBI, or Genomics Browser (UCSC) using the reg. sep #=ONM.000927 or the gene ID ABCB1. With regard to the nomenclature of the polymorphisms it is referred to ABCB1 at chr7:86731406-86940797—(NM_000927) ATP-binding cassette, sub-family B (MDR/TAP), NM #=Reference Sequence Number, Localisation on genome according to The April 2003 human reference sequence (UCSC version hg15) based on NCBI Build 33. All polymorphisms have been selected from the public SNP database of SNP (www.ncbi.nlm.nih.gov/SNP). The location of the SNPs within ABCB, is according to the April 2003 human reference sequence (UCSC version mg 15; www.qenome.ucsc.edu). The more preferred polymorphisms as listed above are described in table 1.

TABLE 1

Polymorphism in the human ABCB1

| Reference Nr. | Position | Sequence |
|---|---|---|
| NM_000927 | 86797791 | AACACNNNNAGAATT[A/T]TGAAGAGGTAT CTGT [SEQ ID NO: 1] |
| NM_000927 | 86763977 | CTCCTTTCTACTGGT[G/A]TTTGTCTTAAT TGGC [SEQ ID NO: 2] |
| NM_000927 | 86748149 | AAAGTACAAGACCCT[G/A]AACTAAGGCAG GGAC [SEQ ID NO: 3] |
| NM_000927 | 86758788 | TAGAGTAAAGTATTC[T/C]AATCAGTGTTA TTTT [SEQ ID NO: 4] |
| NM_000927 | 86731697 | AACACNNNNAGAATT[A/T]TGAAGAGGTAT CTGT [SEQ ID NO: 5] |

TABLE 1-continued

Polymorphism in the human ABCB1

| Reference Nr. | Position | Sequence |
|---|---|---|
| NM_000927 | 86777670 | GCGGTGATCAGCAGT[C/T]ACATTGCACAT CTTT [SEQ ID NO: 6] |
| NM_000927 | 86731143 | CCCAAAACACAGATC[G/A]ATATAAGATTT TAGG [SEQ ID NO: 7] |

The CNS-active medicaments are preferably selected from the group consisting of antidepressants, anxiolytics, hypnotics, cognitive enhancers, antipsychotics, neuroprotective agents, antiemetics, antiepileptics, antibiotics, anticancer agents, antimycetics, antiparkinson agents, antiviral agents, glucocorticoids, immunosuppressants, statins, neuroleptics, and opioids. A preferred class of medicaments are antidepressants. Examples of CNS-active medicaments are described in Schatzberg and Nemeroff, "The American Psychiatric Publishing Textbook of Psychopharmacology", Amer Psychiatric Pr, 2004.

A preferred class of medicaments are antidepressants. Examples of antidepressants are imipramine, amitriptyline, amitriptylinoxide, bupropion, citalopram, clomipramine, doxepine, desipramine, flesinoxan, fluoxetine, fluvoxamine, maprotiline, mirtazapine, mianserin, moclobemide, nefazodone, nortriptyline, paroxetine, selegiline, sertraline, tranylcypromine, trazodone, trimipramine and, venlafaxine. Preferred examples of antidepressants which are substrate of the ABCB1 protein are amitriptyline, citalopram, doxepine, flesinoxan, nortriptyline, paroxetine, trimipramine, and venlafaxine. Especially preferred examples of antidepressants are citalopram, venlafaxine or, paroxetine.

Further preferred CNS-medicaments are anxiolytics, hypnotics, cognitive enhancers and, antipsychotics. Examples of anxiolytics include but are not limited to alprazolam, bromazepam, clonazepam, diazepam, iorazepam, halazepam, chlordiazepoxide, buspirone, azapirone, pagoclone, prazosin, biperiden and, kava kava. Examples of hypnotics are secobarbital, pentobarbital, methaqualone, ethchlorvynol, chloral hydrate, mebrobamate. Examples of cognitive enhancers are acetyl L-carnitine (ALCAR), adrafinil, aniracetam, deprenyl, galantamine, hydergine, idebenone, modafinil, picamilon, piracetam, pyritinol, vasopressin and, vinpocetine. Examples of antipsychotics are risperidon, olanzapine, quetiapine and, ziprasidone, chlorpromazine, fluphenazine, trifluoperazine, perphenazine, thioridazine, haloperidol, thiothixene, molindone, loxapine, clozapine, olanzapine, quetiapine, risperidone, sertindole, ziprasidone, amisulpid, aripriprazol, benperidol, chlorpromazine, chlorprothixen, flupentixol, fluspirilen, levomepromazin, benperidol, melperon, perazin, perphenazin, pimozid, pipamperon, sulpirid, triflupromazin, zotepin, zuclopenthixol.

Further preferred examples of substrates of the ABCB1 protein are antiemetics such as domperidone or ondansetron, antiepileptics such as carbamazepine, felbamate, lamotrigin, phenobarbita and phenyloin, antiparkinson agents such as budipin or L-Dopa, neuroleptics such as olanzapine, quetiapine, risperidone and sulpiride, or opioids such as fentanyl or morphine.

The patients to be tested are human patient suffering, from a disorder which may be treated with a CNS-active medicament, e.g. a psychiatric disorder. Particularly, the patients have a depressive disorder, dysthymia and/or a bipolar disorder.

The present invention relates to the determination of the prognosis of a clinical response in a human patient. The term "a clinical response" in the present application with regard to antidepressants relates to a remission status after six weeks of treatment. Methods of assessing a remission status are well known in the art. For example, remission can be evaluated according to the Hamilton Depression Rating Scale (HAM-D; Hamilton, Br. J. Soc. Clin. Psychol. 6 (1967) 278-296). A HAM-D score of 10 or below is regarded as remission of the depressive symptoms. Remission can also be assessed according to a normalisation of the hypothalamic-pituitary-adrenocortical (HPA) axis. The development and course of depression is causally linked to impairments in the central regulation of the HPA axis. Abnormalities in the HPA axis can be measured using the dexamethasone-suppression test (DST) or the combined dexamethasone/corticotropin-releasing hormone (Dex/CRH) test. Changes in cortisol and/or adrenocorticotropic hormone (ACTH) measurements during the DST or Dex/CRH test are indicative of HPA dysfunction while normalisation of cortisol and or ATCH is indicative of remission (Heuser et al, J. Psychiat. Res. 28 (1994) 341-356; Rybakowski and Twardowska, J. Psychiat. Res. 33 (1999) 363-370; Zobel et al, J. Psychiat. Res. 35 (2001) 83-94; Künzel et al, Neuropsychopharmacology 28 (2003) 2169-2178). Methods and conditions for performing the DST and Dex/CRH test are well known in the art, see for example Heuser et al, J. Psychiat. Res. 28 (1994) 341-356; Künzel et al, Neuropsychopharmacology 28 (2003) 2169-2178. Briefly, individuals may be pre-treated at 23:00 with an oral administration of 1.5 mg dexamethasone. For the DST test, a blood sample may be drawn at 8:00 prior to dexamethasone administration (i.e. pre-dexamethasone) and at 8:00 the morning following dexamethasone administration (i.e. post-dexamethasone). For the Dex/CRH test, a venous catheter may be inserted at 14:30 the day following dexamethasone administration and blood may be collected at 15:00, 15:30, 15:45, 16:00, and 16:15 into tubes containing EDTA and trasylol (Bayer Inc., Germany). At 15:02, 100 mg of human CRH (Ferring Inc., Germany) may be administered intravenously. Measurement of plasma cortisol concentrations may be done according to known methods, e.g. using a commercial radio-immunoassay kit (ICN Biomedicals, USA). Plasma ACTH concentrations may also be measured according to known methods, e.g. using a commercial immunometric assay (Nichols Institute, USA). With regard to other classes of medicaments, the term "clinical response" may be defined as a reduction of the severity of symptoms by over 50% from the severity of symptoms at the beginning of treatment.

The presence of a polymorphism associated with a delayed, partial, sub-optimal or lacking clinical response to a medicament is preferably determined by a genotyping analysis of the human patient. This genotyping analysis frequently comprises the use of polymorphism-specific primers and/or probes capable of hybridizing with the human ABCB1 gene and allowing a discrimination between polymorphisms, particularly SNPs at a predetermined position. For example, the genotyping analysis may comprise a primer elongation reaction using polymorphism-specific primers as described in the examples. The determination of individual polymorphisms may be carried out by mass-spectrometric analysis as described in the examples. A further preferred embodiment comprises a microarray analysis which is particularly suitable for the parallel determination of several polymorphisms. Suitable microarray devices are commercially available.

Based on the results of polymorphism determination a prognosis of a clinical response in a human patient to a CNS-active medicament which is a substrate of the ABCB1 protein can be made. Thus, on the one hand, if the patient to be tested does not have a polymorphism which is associated with an insufficient clinical response to the medicament, a favourable prognosis for a clinical response can be given and the medicament for obtaining the clinical response may be manufactured, prescribed and administered in a standard dose whereby a sufficient clinical response may be expected with high probability. On the other hand, the patient to be tested may have one or a plurality of polymorphisms which are associated with an unfavourable prognosis for a clinical response of the medicament. If such an unfavourable prognosis for a clinical response is given, a modified therapeutic regimen for the patient may be used. For example, the medicament may be administered in a dose which is higher than the standard dose, e.g. by increasing the dose strength and/or the number of doses to be administered per time interval. Further, the formulation of the medicament may be manufactured and adminstered which shows an increased permeation through the blood-brain barrier, e.g. by including a blood-brain barrier permeation aid such as those indicated in Table 2.

TABLE 2

| Inhibitors and modulators of ABCB1 | |
|---|---|
| Antiacids | Fluphenazine |
| Lansoprazole | Haloperidol |
| Omeprazol | Phenothiazine |
| Pantoprazole | Pimozide |
| Antiarrhythmics | Prochlorpernazine |
| Amiloride | Promethazine |
| Amiodarone | Thioridazine |
| Barnidipine | Trifluoperazine |
| Benidipine | Triflupromazine |
| Bepridil | Opioids |
| Digitoxin | Alfentanil |
| Digoxin | Fentanyl |
| Efonidipine | Methadone |
| Niguldipine | Pentazocine |
| Nilvadipine | Sufentanil |
| Propafenone | Surfactants |
| Propranolol | Cremophor EL |
| Quinidine | Triton X-100 |
| Verapamil | Tween 80 |
| Antibiotics | Others |
| Ceftriaxone | Anti-CD19 |
| Clarithromycin | antibody |
| Erythromycin | Azelastine |
| Fucidine | Bromocriptine |
| Josamycin | Chloroquine |
| Ofloxacin | Cholesterol |
| Anticancer | Cyproheptadin |
| agents | Dipyridamole |
| Azidopine | E6 |
| Gramicidine | Emetine |
| Mitomycin C | EP 51389 |
| Quercetin | Flavinoids |
| Valinomycin | Garlic |
| Antidepressants | GF 120918 |
| Amitriptyline | Ginsenoide |
| Citalopram | Grapefruit |
| Desipramine | Green Tea |
| Fluoxetine | Lidocaine |
| Fluvoxamine | Lonafarnib |
| Imipramine | (SCH66336) |
| Maprotiline | Loratadine |
| Nefazodone | Mefloquine |
| Paroxetine | Midazolam |

TABLE 2-continued

Inhibitors and modulators of ABCB1

| | |
|---|---|
| Reboxetine | Nobilitin |
| Sertraline | orange juice-Seville |
| Trimipramine | Piperine |
| Venlafaxine | Probenecid |
| Antiemetics | Progesterone |
| Antiepileptics | Quinacrine |
| Antihypertensive | Quinine |
| agents | RU 486 |
| | |
| Carvedilol | Spironolactone |
| Doxazosin | Terfenadine |
| Felodipine | Tetrandrine |
| Mibefradil | Thyroid Hormones |
| Nifedipine | TNF alpha |
| Nicardipine | Vandate |
| Nitrendipine | XR9576 |
| Reserpine | Yohimbin |
| Antimycotics | Zosuquidar.3HCl |
| | |
| Itraconazole | Rifampin |
| Ketoconazole | GG918 |
| Antiparkinson | Topotecan |
| Antiviral agents | Puromycin |
| | |
| Indinavir | Mithramycin |
| Lopinavir | Mitomycin C |
| Nelfinavir | Calmodulin |
| Ritonavir | inhibitors |
| Saquinavir | Indomethacin |
| Steroids | Quinine |
| Progesterone | Melphalane |
| Immunosuppressants | Econazol |
| | |
| Cyclosporine A | Cholchicin |
| FK 506 | Actinomycin |
| Rapamycin | Taxones |
| Sirolimus | Anthracyclines |
| Tacrolimus | 5'MHC |
| Tamoxifen | Reversin |
| Valspodar (PSC833) | JS-2190 |
| Vinblastine | PGP-4008 |
| Statins | WP631 |
| | |
| Atorvastatin | Dihydropyridine |
| Lovastatin | Quinolines |
| Simvastatin | VX-710 |
| Neuroleptics | S-9788 |
| | |
| Chlorpromazine | |
| Droperidol | |
| Flupenthixol | |

Further, the manufacture and administration of the medicament may be combined with the manufacture and administration of a further medicament which is an inhibitor of the ABCB1 protein. Suitable inhibitors of the ABCB1 protein are known and for example described in US 2003/0073713 A1 which is herein incorporated by reference. Further ABCB1 inhibitors are described in Marzolini C, et al (2004), Clin Pharmacol Ther. 2004 January; 75(1):13-33 which is herein incorporated by reference.

As outlined above, the present invention also relates to diagnostic compositions and kits for the prognosis of a clinical response in a human patient to a CNS-active medicament which is a substrate of the ABCB1 protein. A diagnostic composition or kit preferably comprises at least one primer and/or probe for determining at least one polymorphism which is associated with a lack of clinical response to the CNS-active medicament. The primers and/or probes may be nucleic acid molecules such as a DNA, an RNA or nucleic acid analogues such as peptide nucleic acids (PNA) or a locked nucleic acids (LNA). The primer and/or probes are selected such that they can discriminate between polymorphisms at the position to be analyzed. Usually, the primers and probes have a length of at least 10, preferably at least 15 up to 50, preferably up to 30 nucleic acid building blocks, e.g. nucleotides. In a preferred embodiment, the composition or kit comprises at least one primer which hybridizes to the human ABCB1 gene under predetermined conditions, e.g. of temperature, buffer, strength and/or concentration of organic solvent, and which allows a specific determination of the polymorphism to be tested. Preferred examples of such primers are indicated in Table 3 and Table 4 for genotyping with a mass array system and in Table 5 for genotyping rs2235015 with hybridisation probes."

TABLE 3

Primer sequence for SNP amplification and sequencing

| SNP | PCR Forward | PCR Reversed |
|---|---|---|
| rs2235015 | ACGTTGGATGCACCTAGA CCACCACAAAAC [SEQ ID NO: 8] | ACGTTGGATGAAAACTG AGTCAGTTCGACC [SEQ ID NO: 9] |
| rs2235040 | ACGTTGGATGACTGGAGC ATTGACTACCAG [SEQ ID NO: 10] | ACGTTGGATGTTAGTTT CATGCTGGGGTCC [SEQ ID NO: 11] |
| rs2235067 | ACGTTGGATGAGTGGAGA AAGTGCTCGAAG [SEQ ID NO: 12] | ACGTTGGATGTTCTACC TCAGAGATGTCCC [SEQ ID NO: 13] |
| rs2032583 | ACGTTGGATGCTGGGAAG GTGAGTCAAAC [SEQ ID NO: 14] | ACGTTGGATGGCATAGT AAGCAGTAGGGAG [SEQ ID NO: 15] |
| rs17064 | ACGTTGGATGGACTCTGA ACTTGACTGAGG [SEQ ID NO: 16] | ACGTTGGATGGTGAACT CTGACTGTATGAG [SEQ ID NO: 17] |
| rs2032588 | ACGTTGGATGTGATGCAG AGGCTCTATGAC [SEQ ID NO: 18] | ACGTTGGATGGGCAACA TCAGAAAGATGTG [SEQ ID NO: 19] |
| rs1055302 | ACGTTGGATGTCCACATT AAGGTGGCTCTC [SEQ ID NO: 20] | ACGTTGGATGTCATAAT TGTGCCTCACCCC [SEQ ID NO: 21] |

TABLE 4

Primer sequence for primer extension systems

| SNP | Extension Primer | Stop Mix |
|---|---|---|
| rs2235015 | ACCACCACAAAACAAACATA [SEQ ID NO: 22] | CGT |
| rs2235040 | TGCCTCCTTTCTACTGGT [SEQ ID NO: 23] | ACT |
| rs2235067 | AGAGAAAGTACAAGACCCT [SEQ ID NO: 24] | ACT |
| rs2032583 | AATTAAGTAGAGTAAAGTATTC [SEQ ID NO: 25] | ACG |
| rs17064 | AATGTTAAACAGATACCTCTTCA [SEQ ID NO: 26] | CGT |
| rs2032588 | CTGCGGTGATCAGCAGT [SEQ ID NO: 27] | ACG |
| rs1055302 | CAAACCCAAAACACAGATC [SEQ ID NO: 28] | ACT |

TABLE 5

Primers used for genotyping with hybridization probes for rs2235015

| | Description | Hybridisation probes |
|---|---|---|
| PCR Primer Forward | ABCB1 | CAATTAAAACTgAgTCAgTTCg [SEQ ID NO: 29] |
| PCR Primer Reverse | ABCB1 | TTTTAAACATTTCTACAACTTgATg [SEQ ID NO: 30] |
| Anchor Probe | rs2235015 | TgTATCATTgATATCACCTAgACCA CCAC-FL [SEQ ID NO: 31] |
| Sensor Probe | Sensor[G] | LCRed640-AAACAAACATAC CATTTATgTCTCT-PH [SEQ ID NO: 32] |

The use of the hybridisation probes disclosed in Table 5 enables sequence-specific detection of PCR products. These hybridisation probes consist of two different oligonucleotides that hybridize to an internal sequence of the amplified fragment during the annealing phase of PCR. One probe is labeled at the 5' end with a fluorophore. The other probe is labeled at the 3' end with e.g. fluorescein. After hybridization to the target sequence, the two probes produce Fluorescence Resonance Energy Transfer (FRET). The emitted fluorescence is measured. This technique can be used for quantification and genotyping. For example, genotyping can be performed with melting curve analysis. Table 5 shows the PCR primer and the dyes labeled hybridisation probes for a genotyping test of rs2235015.

The composition or kit preferably further comprises an enzyme for primer elongation such as a DNA polymerase, nucleotides, e.g. chain elongation nucleotides such as deoxide nucleoside triphosphates (dNTPs) or chain termination nucleotides such as dideoxynucleoside triphosphates (ddNTPs) and/or labelling groups, e.g. fluorescent or chromogenic labelling groups.

A microarray for the prognosis of a clinical response to a CNS-active medicament comprises a carrier, e.g. a planar carrier or a microchannel device, having immobilized thereto at least one probe which allows a determination of a polymorphism to be tested. Preferably, the microarray carrier has immobilized thereto a plurality of different probes located at different areas on the carrier which are designed such that they can bind nucleic acid molecules, e.g. RNA molecules or DNA molecules, amplification products, primer elongation products, etc. containing the sequence in which the polymorphism to be tested is located. Thus, an identification of the polymorphism to be analyzed by detection of a site-specific binding events of the nucleic acid sample molecule to the probe immobilized on the carrier may be accomplished.

Finally, the present invention relates to a therapeutic composition or kit comprising a CNS-active medicament which is a substrate of the ABCB1 protein in a therapeutically effective dose and a further medicament which is an inhibitor of the ABCB1 protein in a therapeutically effective dose for treating a human patient having at least one polymorphism in the ABCB1 gene associated with a lack of clinical response to said CNS-active medicament. The medicaments may be present as a single formulation or as separate formulations, if desired. Pharmaceutically acceptable carriers, diluents or adjuvants may be included. The composition or kit may be administered by any suitable route, e.g. by oral or parenteral administration or any other suitable means.

The schedule of administration and dose of a CNS-active medicament such as, for example an antidepressant drug can vary between patients and are well know in the medical art, see, for example Benkert and Hippius, "Kompendium der Psychiatrischen Pharmakotherapie", Springer Verlag Publishing, 2000; Albers, "Handbook of Psychiatric Drugs: 2001-2002 Edition", Current Clinical Strategies Publishing, 2000. For antidepressants, there are three therapeutic possibilities for individuals that have been genotyped with a SNPs in the ABCB1 gene.

1. The dosage of an antidepressant that is a substrate of ABCB1 would be increased. Examples of such antidepressants are, between 10 mg and 100 mg per day, preferably 40 mg, citalopram; between 10 mg and 80 mg per day, preferably 20 mg, paroxetine; between 50 mg and 500 mg per day, preferably 150 mg, venlafaxine; between 25 mg and 300 mg per day, preferably 75 mg, amitriptyline; between 25 mg and 400 mg per day, preferably 75 mg, nortriptyline; between 50 mg and 400 mg per day, preferably 200 mg, fluvoxamine; between 2 mg and 15 mg per day, preferably 10 mg, reboxetine.

2. An alternative antidepressant that is not a substrate of ABCB1 would be administered. Preferred examples include between 15 mg and 100 mg per day, preferably 30 mg, mirtazapine; between 5 mg and 80 mg per day, preferably 20 mg, fluoxetine.

3. An antidepressant that is a substrate of ABCB1 would be combined with an inhibitor or modulator of ABCB1. Examples of inhibitors or modulators of ABCB1 are disclosed in Table 2 and the dosage would be determined according to the manufactures recommendations.

Furthermore, the present invention shall be explained by the following Tables and Figures as well as Examples:
Table and Figure Legend:

TABLE 6

Location according to the April 2003 human reference sequence (UCSC version hg15) (www.genome.ucsc.edu/), heterozygosity and p-values of the Hardy-Weinberg equilibrium of ABCB1 SNPs.

| SNP ID | location within gene | function | location hg15 | Heterozygosity | p-value HWE |
|---|---|---|---|---|---|
| rs1055305 | 3' | 3' | 86730918 | 0.00 | NA |
| rs1055302 | 3' | 3' | 86731143 | 0.23 | 0.79 |
| rs17064 | exon 29 | 3'UTR | 86731697 | 0.11 | 0.71 |
| rs2235051 | exon 29 | 3'UTR | 86731882 | 0.00 | NA |
| rs1045642 | exon 27 | Ile/Ile | 86736872 | 0.50 | 1.00 |
| rs2235045 | intron | intronic | 86743871 | 0.00 | NA |
| rs2235044 | exon 25 | Pro/Pro | 86744052 | 0.00 | NA |
| rs2235067 | Intron 23 | intronic | 86748149 | 0.20 | 0.53 |
| rs4148744 | intron | intronic | 86749001 | 0.08 | 1.00 |
| rs4148743 | intron | intronic | 86749317 | 0.53 | 0.049 |
| rs2032583 | Intron 22 | intronic | 86758788 | 0.18 | 0.34 |
| rs2032582 | exon 22 | Ala/Ser/Thr* | 86758845 | 0.54 | 0.53 |
| rs2032581 | intron | intronic | 86759037 | 0.00 | NA |
| rs2235040 | Intron 21 | intronic | 86763977 | 0.20 | 0.57 |
| rs2235039 | exon 21 | Val/Met | 86764081 | 0.00 | NA |
| rs1922242 | intron | intronic | 86771894 | 0.53 | 0.06 |
| rs2235035 | intron | intronic | 86777313 | 0.47 | 0.67 |
| rs2032588 | Intron 13 | intronic | 86777670 | 0.1 | 1.00 |
| rs2229109 | exon 12 | Ser/Asn | 86778036 | 0.1 | 0.69 |
| rs2235030 | intron | intronic | 86778153 | 0.00 | NA |
| rs2235029 | intron | intronic | 86778162 | 0.00 | NA |
| rs2235023 | intron | intronic | 86788679 | 0.13 | 0.51 |
| rs2235022 | exon 9 | Glu/Glu | 86788904 | 0.00 | NA |
| rs1202168 | intron | intronic | 86794189 | 0.48 | 0.75 |
| rs1202167 | intron | intronic | 86795286 | 0.51 | 0.32 |
| rs2235019 | intron | intronic | | 0.02 | 1.00 |
| rs2235018 | intron | intronic | 86797592 | <0.01 | 1.00 |
| rs2235017 | intron | intronic | 86797600 | <0.01 | 1.00 |
| rs2235016 | intron | intronic | 86797639 | 0.00 | NA |
| rs2235015 | intron 5 | intronic | 86797791 | 0.28 | 1.00 |
| rs2235014 | intron | intronic | 86797842 | 0.00 | NA |

TABLE 6-continued

Location according to the April 2003 human reference sequence (UCSC version hg15) (www.genome.ucsc.edu/), heterozygosity and p-values of the Hardy-Weinberg equilibrium of ABCB1 SNPs.

| SNP ID | location within gene | function | location hg15 | Hetero-cygosity | p-value HWE |
|---|---|---|---|---|---|
| rs1202179 | intron | intronic | 86802506 | 0.44 | 0.41 |
| rs1989831 | intron | intronic | 86803706 | 0.43 | 0.34 |
| rs1202172 | intron | intronic | 86809201 | 0.39 | 1.00 |
| rs1202171 | intron | intronic | 86809272 | 0.43 | 0.41 |
| rs4148733 | intron | intronic | 86811459 | 0.27 | 0.12 |
| rs1202186 | intron | intronic | 86811485 | 0.45 | 0.41 |
| rs1202185 | intron | intronic | 86811611 | 0.43 | 0.42 |
| rs1202183 | exon 5 | Asn/Ser | 86813210 | 0.00 | NA |
| rs1202182 | intron | intronic | 86813531 | 0.44 | 0.42 |
| rs1202181 | intron | intronic | 86814377 | 0.42 | 0.89 |
| rs2235074 | intron | intronic | 86823273 | 0.08 | 0.34 |
| rs2214102 | exon 3 | TLI | 86827728 | 0.13 | 0.26 |
| rs3213619 | exon 2 | 5'UTR | 86828420 | 0.00 | NA |
| rs2188524 | intron | intronic | 86828662 | 0.00 | NA |
| rs4148731 | intron | intronic | 86837556 | 0.06 | 1.00 |
| rs4148730 | intron | intronic | 86837578 | 0.06 | 0.49 |
| rs4604363 | intron | intronic | 86852423 | 0.00 | NA |
| rs2157928 | intron | intronic | 86856631 | 0.00 | NA |
| rs4148729 | intron | intronic | 86860613 | 0.06 | 0.041 |
| rs2157926 | intron | intronic | 86868727 | 0.12 | 1.00 |
| rs4148728 | intron | intronic | 86869044 | 0.00 | NA |
| rs916715 | intron | intronic | 86925156 | 0.00 | NA |
| rs2188529 | intron | intronic | 86930698 | 0.04 | 0.33 |
| rs3747802 | promoter | intronic | 86940813 | 0.00 | NA |
| rs4148727 | promoter | promoter | 86942971 | 0.06 | 0.041 |

*the frequency of the rare third allele A = 4.8%, present either as GA (3.2%) or TA (1.6%), the frequency of the GT genotype is 49.2%.

TABLE 7 p-values of the association of ABCB1 SNPs with remission status after 6 weeks of treatment in all patients, patients treated with citalopram/venlafaxine/paroxetine and patients treated with mirtazapine (Abbreviation: n.s. = not significant).

| SNP ID | all patients | patients treated with citalopram/venlafaxin/paroxetin | Patients treated with mirtazapine |
|---|---|---|---|
| *rs1055302 | n.s | 0.045 | n.s |
| *rs17064 | n.s | 0.025 | n.s |
| rs1045642 | n.s | n.s | n.s |
| *rs2235067 | n.s | 0.009 | n.s |
| rs4148744 | n.s | n.s | n.s |
| rs4148743 | n.s | n.s | n.s |
| *rs2032583 | n.s | 0.017 | its |
| rs2032582 | n.s | n.s | n.s |
| rs2235040 | n.s | 0.002 | n.s |
| rs1922242 | n.s | n.s | n.s |
| rs2235035 | n.s | n.s | n.s |
| rs2032588 | n.s | 0.028 | n.s |
| rs2229109 | n.s | n.s | n.s |
| rs2235023 | n.s | n.s | n.s |
| rs1202168 | n.s | n.s | n.s |
| rs1202167 | n.s | n.s | n.s |
| rs2235019 | n.s | n.s | n.s |
| rs2235018 | n.s | n.s | n.s |
| rs2235017 | n.s | n.s | n.s |
| rs2235015 | 0.015 | 0.00007 | n.s |
| rs1202179 | n.s | n.s | n.s |
| rs1989831 | n.s | n.s | n.s |
| rs1202172 | n.s | n.s | n.s |
| rs1202171 | n.s | n.s | n.s |
| rs4148733 | n.s | n.s | n.s |
| rs1202186 | n.s | n.s | n.s |
| rs1202185 | n.s | n.s | n.s |
| rs1202183 | n.s | n.s | n.s |
| rs1202182 | n.s | n.s | n.s |
| rs1202181 | n.s | n.s | n.s |
| rs2235074 | n.s | n.s | n.s |
| rs2214102 | 0.02 | n.s | n.s |
| rs3213619 | n.s | n.s | n.s |
| rs2188524 | n.s | n.s | n.s |
| rs4148731 | n.s | n.s | n.s |
| rs4148730 | n.s | n.s | n.s |
| rs4604363 | n.s | n.s | n.s |
| rs2157928 | n.s | n.s | n.s |
| rs4148729 | n.s | n.s | n.s |
| rs2157926 | n.s | n.s | n.s |
| rs4148728 | n.s | n.s | n.s |
| rs916715 | n.s | n.s | n.s |
| rs2188529 | n.s | n.s | n.s |
| rs3747802 | n.s | n.s | n.s |
| rs4728711 | n.s | n.s | n.s |

*For these SNPs the association was performed in a larger sample (284 total patients; 98 treated with citalopram/venlafaxine/paroxetine; 74 treated with mirtazapin).

TABLE 8

Description of the experimental procedures of the animal experiments.

| | Citalopram | Mirtazapine | Venlafaxine |
|---|---|---|---|
| Animals | | | |
| Gender | male | male | male |
| Group size [n] | 8 | 9 | 8 |
| Age [weeks] | 16-24 | 15-17 | 12-15 |
| Weight abcb1ab (−/−) | 31.2 ± 0.6 | 28.6 ± 0.3 | 30.6 ± 0.5 |
| Weight abcb1ab (+/+) | 29.8 ± 1.0 | 28.3 ± 0.6 | 29.9 ± 1.0 |
| Experimental procedures | | | |
| s.c. administerion via osmotic pumps | 60 µg/day | 60 µg/day | 300 µg/day |
| Extraction procedure | | | |
| Isoamylalcohol (plasmaextraction) | 0% | 0% | 0.5% |
| Isoamylalcohol (organextraction) | 0% | 0% | 0.5% |
| High-performance liquid chromatography | | | |
| Mobile phase gradient [% B] | 5-25 | 0-25 | 0-30 |
| Detection UV [nm] | 214 | 214 | 214 |
| Detection fluorescence ex/em [nm] | 230/300 | 295/370 | 225/305 |

FIG. 1

Cerebrum/plasma ratios of drug concentration in abcb1ab (−/−) mice compared to wild-type controls.

After 11 day continuous sub-cutaneous administration of venlafaxine, mirtazapine and citalopram, no differences in plasma levels of these drugs, including d-venlafaxine the major metabolite of venlafaxine, were found between abcb1ab (−/−) mutant and their wildtype littermates. Drug and metabolite concentrations were also not different between mutant and wildtype littermates in those organs that do not have a blood-organ barrier. These include liver, spleen, kidney and lung (data not shown). There were, however, significant differences in the cerebrum/plasma ratios of citalopram, venlafaxine and its metabolite d-venlafaxine but not in the cerebrum/plasma ratios of mirtazapine. For citalopram ($F_{6,9}=39.1$; $p<0.001$) there was a 3 fold higher concentration in the brain of abcb1ab (−/−) mutant compared to wildtype animals. For venlafaxine ($F_{6,9}=32.1$; $p<0.001$) and its metabolite d-venlafaxine ($F_{6,9}=3.8$; p=0.035) abcb1ab (−/−) mutant presented 1.7 and 4.1 fold higher concentrations in the brain. For mirtazapine, no significant differences in cerebrum/plasma ratios were observed. Significant but smaller drug-dependent differences similar to those in the brain were observed for testes, another organ with a blood/organ barrier (data not shown).

*=p<0.05; **=p<0.001.

FIG. 2

Representation of linkage disequilibrium (LD) structure in ABCB1 using D' as a measure for the strength of LD.

FIG. 3

% of patients in remitters (grey bars) and non-remitters (white bars) according to the rs2235015 genotype for patients treated with citalopram/venlafaxine/paroxetine (substrates) (3B) and mirtazapine (3A).

FIG. 4

Drug dose and plasma levels of antidepressants according to rs2235015 genotype.
Part A: administered mean drug dose administered in weeks 4-6 of antidepressant treatment in mg.
Part B: mean plasma levels of administered antidepressants for weeks 4-6 of antidepressant treatment in ng/ml. For GG homozygotes, plasma venlafaxine levels were 356.5 ng/ml (SEM=51.6).
Mirtazapine N=65, citalopram N=35, paroxetine N=29, venlafaxine N=22.

1. METHODS

1.1 Experiments-Using Transgenic Animals

Materials

Venlafaxine and o-desmethylvenlafaxine (d-venlafaxine) was obtained from Wyeth-Pharma GmbH (Münster, Germany). Mirtazapine was obtained from Thiemann Arzneimittel GMBH (Waltrop, Germany) and citalopram from Lundbeck (Copenhagen, Denmark). Protriptyline was purchased from RBI (Massachusetts, USA). All other chemicals were obtained in the purest grade available from Merck (Darmstadt, Germany).

Animals

All animal experiments were conducted in accordance with the Guide for the Care and Use of Laboratory Animals of the Government of Bavaria, Germany.

Male abcb1ab(−/−) mice and FVB/N wildtype mice were housed individually and maintained on a 12:12 h light/dark cycle (lights on at 07:00), with food and water ad libitum. Abcb1ab double knockout mice, originally created by A. Schinkel by sequential gene targeting in 129/Ola E14 embryonic stem cells[28] and backcrossed seven times (N7) to FVB/N from the C57BL/6×129 chimera, and FVB/N wildtype mice were received from Taconic (Germantown, USA; FVB/Tac-[KO]Pgy2 N7). A homozygous colony is maintained at the Max-Planck Institute of Psychiatry on the N7 FVB/N background through intercrossing of homozygous mice. Age, weight and group size of the used mice are shown in Table 3.

1.2 Experimental and extraction procedures

Experimental and extraction procedures were performed as described before[12,26]. Citalopram, mirtazapine and venlafaxine dissolved in 0.9% sodium chloride and 0.5% ethanol was administered subcutaneously in the nape of the neck through surgically implanted osmotic infusion pumps (ALZET™ micro-osmotic pump, Alza corporation, Palo Alto, USA), which continuously delivered the drugs in the scheduled concentrations (table 1). After 11 days, the mice were anesthetized and sacrificed. The dissected organs were homogenized and a liquid-liquid extraction procedure has been carried out with n-hexan/isoamylalcohol (Table 3) in the first step and phosphoric acid in the second. The extraction recoveries were >90% for citalopram, mirtazapine, venlafaxine and 36% for d-venlafaxine.

1.3 High-Performance Liquid Chromatography

HPLC measurements were performed as described before[12,26]. A Beckman gradient pump, autoinjector, UV detector and a Merck fluorescence detector, were used for the high-performance liquid chromatography analysis. Separations were made on a reversed phase Luna 5μ C18(2) 250×4.6 mm column (Phenomenex, Torrance, USA), 60° C., mobile phase flow 1 ml/min. A mobile phase gradient with acetonitrile was used for the chromatography analysis (Table 3). The substances were determined by UV absorption and fluorescence at the described wavelength (Table 3).

1.4 Human Genetics

Patients 255 patients admitted to our psychiatric hospital for treatment of a depressive disorder presenting with a single or recurrent major depressive episode, dysthymia or bipolar disorder as their primary psychiatric diagnoses were recruited for the study. Patients were included in the study within 1-3 days of admission to our hospital and the diagnosis was ascertained by trained psychiatrists according to the Diagnostic and Statistical Manual of Mental Disorders (DSM) IV criteria. Depressive disorders due to a medical or neurological condition were an exclusion criterion. Ethnicity was recorded using a standardized self-report sheet for perceived nationality, mother language and ethnicity of the subject itself and all 4 grandparents. All included patients were Caucasian and 92% of German origin. The study has been approved by the local ethical committee. Written informed consent was obtained from all subjects.

Controls:

339 healthy, age-, sex- and ethnicity-matched controls were selected randomly from a Munich-based community sample and their genotypes used in the construction of a linkage disequilibrium map of ABCB1. Recruitment of controls was also approved by the local ethics committee and written informed consent was obtained from all subjects.

Psychopathology and Definition of Response to Antidepressant Drug Treatment:

In 255 patients severity of psychopathology was assessed using the 21 items Hamilton Depression-Rating Scale (HAM-D) by trained raters. Ratings were performed within 3 days of admission and then in weekly intervals until discharge. Remission of depressive symptoms was defined as reaching an overall HAM-D score≦8. Patients were subdivided according to their remission status after 6 weeks of hospitalization. All patients were treated with antidepressant drugs within a few days of admission. The type antidepressant medication was not influence by the participation in the study, but chosen freely by the responsible psychiatrist. For all patients plasma concentration of antidepressant medication was monitored to assure clinically efficient drug levels. For patients treated with citalopram, paroxetine, venlafaxine or mirtazapine the mean administered drug dose in mg and drug plasma concentration in ng/ml over treatment weeks 4-6 were calculated.

Plasma Concentration of Antidepressant Drugs:

Plasma citalopram, mirtazapine, and paroxetine were extracted with a liquid-liquid extraction procedure and that measured after HPLC with UV absorption and fluorescence. For this 100 µl internal standard (protriptyline 2 µg/ml), 1000 µl sodium hydrogencarbonate (2M, pH 10.5, and 5 ml n-hexan with 1.5% isoamylalcohol was add to 1000 µl plasma. After shaking for 20 min and centrifugation 15 min 4000 r.p.m. the organic phase were transferred in 250 µl 0.85% phosphoric acid. The sample were again shaken for 20 min, centrifugated 15 min 4000 r.p.m., and the lower watery phase analyzed in the HPLC.

We used a reversed phase Luna 5µ C18(2) 250×4.6 mm column (Phenomenex, Torrance, USA), 60° C., mobile phase flow 1 ml/min. A mobile phase gradient with acetonitrile and phosphoric acid (1.5 ml 85% $H_3PO_4$/l, pH=3.5, adjusted with NaOH) was used for the chromatography analysis (mirtazapine 5-33% acetonitrile in 30 min; citalopram and paroxetine 28-35% acetonitrile in 45 min). The substances were determined by UV absorption (214 nm) and fluorescence at the suitable wavelength (citalopram 235/300 nm, mirtazapine 295/370 nm, paroxetine 295/365 nm, protriptyline 295/420 nm). The extraction recovery was >90%, and the intra and inter day variation coefficient was <10%.

DNA Preparation:

On enrollment in the study, 40 ml of EDTA blood were drawn from each patient and DNA was extracted from fresh blood using the Puregene® whole blood DNA-extraction kit (Gentra Systems Inc; MN).

SNP Selection and Genotyping:

26 ABCB1 SNPs were selected from dbSNP (www.ncbi.nlm.nih.gov:80/). The SNP search tool at (ihg.gsf.de/ihg/snps.html) was used to download SNP sequences from public databases. Genotyping was performed on a MALDI-TOF mass-spectrometer (MASSARRAY® system) employing the Spectrodesigner software (Sequenom™; CA) for primer selection and multiplexing and the homogeneous mass-extension (hMe) process for producing primer extension products. All primer sequences are available upon request. The tri-allelic SNP rs2032582 was measured in the light-cycler using allele-specific hype-probes (primer sequences available on request).

1.3 Statistical Analysis

Animal Experiments:

Statistical analysis was carried out the statistic software SPSS 10.0 for windows (Chicago, Ill.). Significance was tested by one-factorial multivariate analyses of variance (MANOVAs). Univariate F-tests followed to identify the variables whose differences between the two groups contributed significantly to the global group effect. As a nominal level of significance α=0.05 was accepted and corrected (reduced according to the Bonferroni procedure) for all a posteriori tests (univariate F-tests) in order to keep the type I error less than or equal to 0.05.

Human Genetics:

All analyses for binary outcomes were performed using logistic regression using both R and SPSS (version 11), as well as by exact contingency table analyses using SPSS. The tables were constructed as tests per genotype, i.e. for a given binary outcome and a single SNP we analyzed a 2*3 table with 2 d.f. For the tri-allelic SNP rs2032582 (G/T/A) a 2*5 table with 4 d.f. was used. To detect any genotype dependent differences in antidepressant dose or plasma level, we used a one-way ANOVA with the genotype of rs2235015 as factor.

For haplotype analyses individual haplotype assignments were determined using SNPHAP (www.gene.cimr.cam.ac.uk/clayton/software/snphap.txt). Only haplotype assignments with an uncertainty of less than five percent and a frequency of over five percent were included in the analyses. For the analysis of the LD pattern and computing of pairwise D' values from genotype data of our sample of cases and controls, we used the R package "genetics" (lib.stat.cmu.edu/R/CRAN/). Haplotype block definition was done using the |D'| method (Lewontin R. C., On Measures of Gametic Disequilibrium, Genetics 120: 849-852 (November, 1988)) with a threshold of 0.75. For graphical depiction of LD we used GOLD (www.sph.umich.edu/csg/abecasis/publications/10842743.html), GOLD—graphical overview of linkage disequilibrium. Abecasis G R and Cookson W O. Bioinformatics (2000) 16:182-3). SNPs with a frequency of the minor allele less than 0.1 were omitted from the LD analysis.

2. RESULTS 2.1 Differential Regulation of Intracerebral Levels of Mirtazapine, Venlafaxine and Citalopram in abcb1a and abcb1b Double Knock-Out Mice.

While p-glycoprotein is encoded by a single gene in humans (ABCB1) there are two homologues in mice, the abcb1a (also called mdr1a or mdr3) and abcb1b (also called mdr1b or mdr1) genes[9]. Although abcb1a and abcb1b are not always expressed in the same organs, the overall distribution of these genes in mouse tissue coincides roughly with that of the single ABCB1 gene in humans, suggesting that abcb1a and abcb1b together function in the same manner as human ABCB1[10,11]. We could previously show that several antidepressants are substrates of p-glycoprotein following a singe drug administration[12,26,27]. We selected three of them to test whether this substrate-specificity remains after subchronic treatment, which is more relevant for the clinical situation. Using transgenic mice lacking abcb1a and abcb1b, we could show that following administration for 11 days the intracerebral concentrations of the antidepressant drugs citalopram (belonging to the class of selective serotonin reuptake inhibitors) and venlafaxine (a combined serotonin and norepinephrine reuptake inhibitor) and its active metabolite desmethyl-venlafaxine, are regulated by p-glycoprotein. This is not the case for mirtazapine, an antidepressant drug mainly targeting serotonin (5-HT)2C and alpha2A-adrenergic receptors (see FIG. 1).

2.2 ABCB1 SNPs are Associated with Remission to Antidepressant Treatment

Since p-glycoprotein regulates access to the brain for some antidepressants, functional polymorphisms in this gene might influence intracerebral antidepressant concentration and thus clinical response to antidepressant drugs. If certain polymorphisms were to alter intracerebral concentrations of specific antidepressants, prior knowledge of the patients' relevant p-glycoprotein genotypes could prevent the administration of a drug that fails to reach therapeutic intracerebral levels despite a plasma concentration that is regarded as clinically sufficient. To test this hypothesis, we first investigated whether SNPs in the ABCB1 gene are associated with clinical drug response. Secondly we analyzed if the association of ABCB1 SNP genotypes with antidepressant response depends on whether or not the drug is a substrate of the ABCB1 gene product. The latter distinction was based on cerebral drug concentrations in mice lacking the respective drug transporter encoding genes. Citalopram, venlafaxine and paroxetine but not mirtazapine were considered as substrates of p-glycoprotein (see data presented in this manuscript and[12] where paroxetine is identified as a substrate of p-glycoprotein).

Of 56 investigated SNPs in ABCB1, 38 turned out to be polymorphic in our sample (Table 6). SNPs were initially spaced with an average intermarker distance of 8.3 kb spanning 209 kb of the gene from the promoter region to exon 29. The average intermarker distance of the informative SNPs was 11.7 kb, spanning 199 kb of the gene (intron 1 to exon 29). All polymorphic SNPs were then tested for association with remission status at 6 weeks in all 255 depressed patients. Remission was defined as reaching a total score smaller or equal to 8 on the Hamilton Depression Rating scale (see method for more detail). We found a significant association with remission ($p<0.05$) for 7 SNPs: rs 1055302, rs 17064, rs 2235067, rs 2032583, rs 2235040, rs 2032588 and rs2235015 (see Table 7). To investigate if the association with remission status depends on whether the antidepressant drug received by the patients was a potential substrate of the human ABCB1, we subgrouped patients according to their antidepressant medication in the first 6 weeks of treatment. The first group of patients had received substrates of abcb1ab: citalopram, paroxetine or venlafaxine as antidepressant treatment within the first 6 weeks (n=86) and the second mirtazapine (n=65), which intracerebral concentration was not found to be regulated by abcb1ab in the mouse knockout model. An association analysis with remission status in the first group of patients revealed significant associations with rs 2235015, rs2235040, rs2235067, rs2032583, rs17064, rs2032588, and rs1055302, the first SNP showing the strongest association ($p<0.00008$). In the patient group receiving mirtazapine no significant association with any of the tested SNPs could be detected (see Table 7). The odds ratios for the association for remission within six weeks with rs2235015 genotype, were 2.056 (95% CI=1.27-3.32) for all patients, 6.15 (95% CI=2.54-14.67) for patients treated with citalopram/paroxetine/venlafaxine and 1.83 (95% CI=0.73-4.55) for patients treated with mirtazapine.

2.3 Haplotype Analysis and Linkage Disequilibrium Mapping

Figure 2:
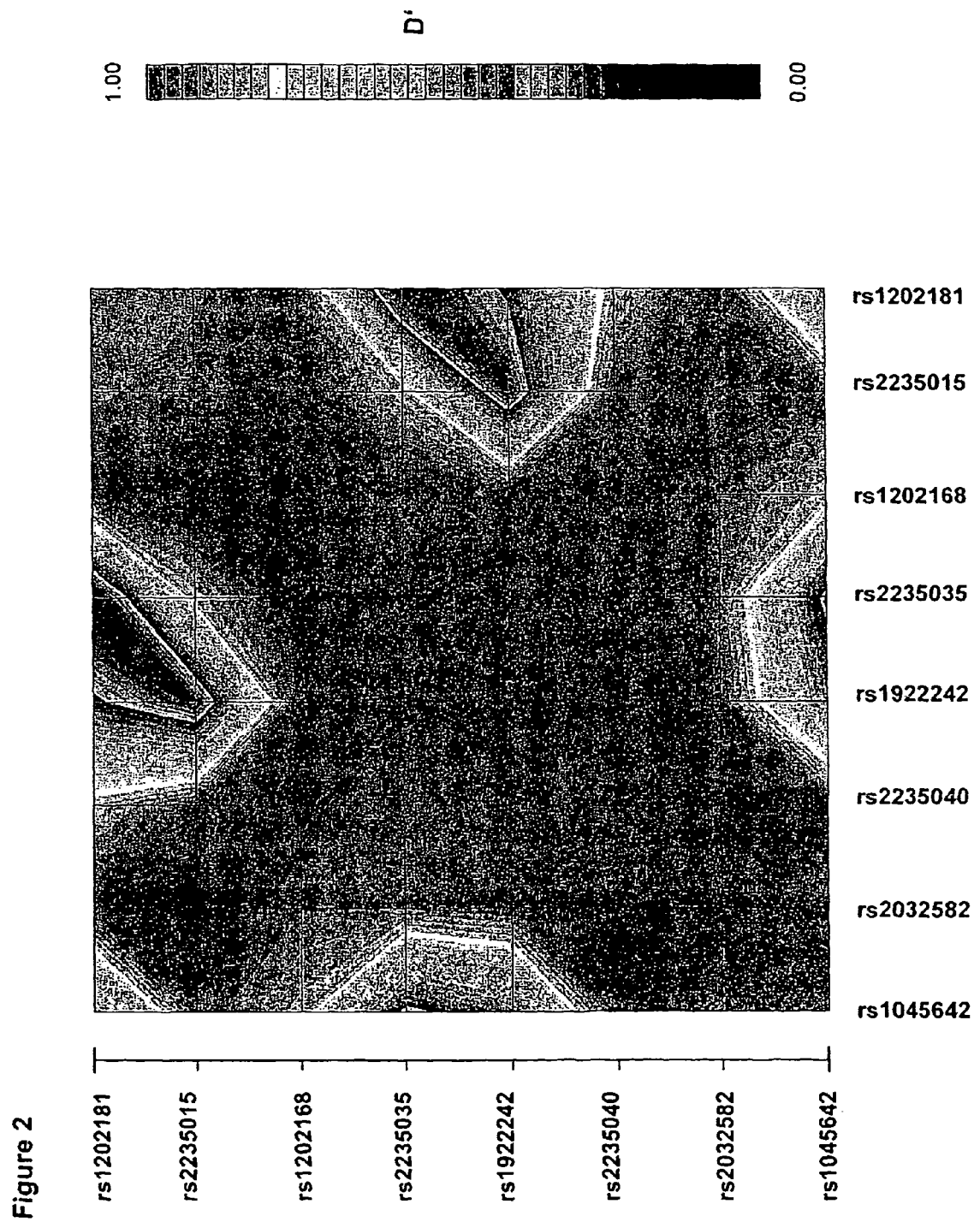

We then constructed all possible haplotypes for polymorphic SNPs genotyped within ABCB1 and repeated the association analysis with remission status for the three patient groups (all patients, patients receiving substrates of abcb1ab and patients receiving mirtazapine). Even though some haplotypes showed a higher OR in the first two patient groups, the association was not statistically significantly different from rs2235015, as the confidence intervals overlapped, suggesting that most of the association is carried by this SNP. Paralleling the single SNP data, no haplotype association was found in the patient group having received mirtazapine. To possibly narrow down the region of ABCB1 containing the causal variant, we analyzed the linkage disequilibrium (LD) block structure of the investigated SNPs within ABCB1 using genotypes of all cases as well as 339 healthy controls. Similar to previous reports in the literature[13,14], we only detected one haplotype block, spanning the examined region of ABCB1 (see FIG. 2). It is thus difficult to pinpoint rs2235015 or any other SNP as the potential causal mutation. Careful characterisation of the functional consequences of the investigated SNPs and the resulting haplotypes in vitro and in vivo are warranted in order to narrow in on the potential causal polymorphism or combination of polymorphisms.

Figure 3:
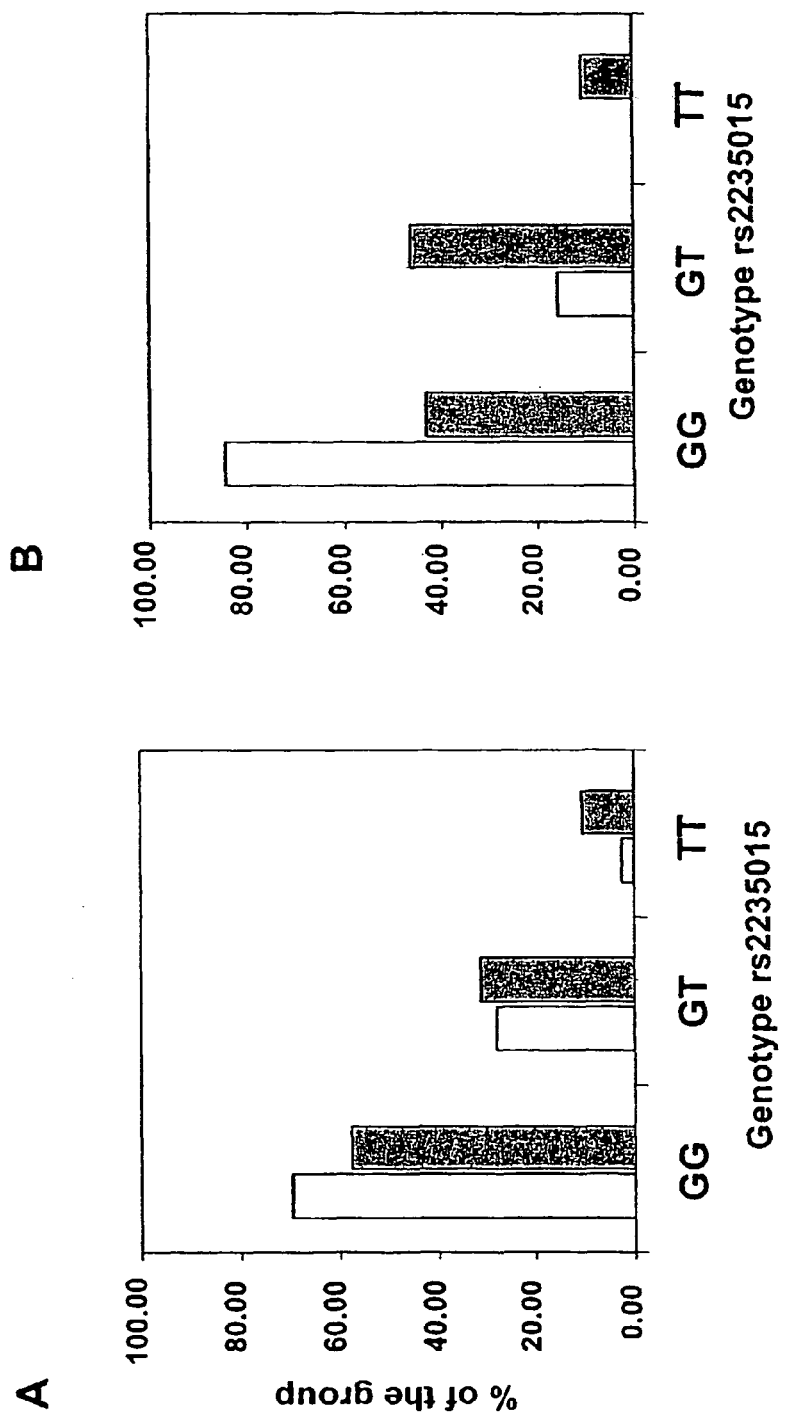

2.4 Use of rs2235015 Genotype for Prediction of Remission to Antidepressant Treatment To evaluate whether the knowledge of the ABCB1 SNP genotypes would allow predicting remission after six weeks of treatment, a discriminant analysis of rs2235015 genotype (group variable) and the remission status at six weeks (independent variable) in patients treated with citalopram/paroxetine/venlafaxine was employed, which showed an overall significant discriminant power of this SNP; Wilks lambda=0.792; $X^2=19.4$; $df=1$; $p=1.0\times10^{-5}$. Using this polymorphism, 75.6% of patients receiving substrates of ABCB1 were correctly classified in remitters and non-remitters, remission being defined as having reached a HAM-D score equal to or smaller than 8 after 6 weeks of treatment. In the patient group treated with mirtazapine, no significant discriminant power of this SNP could be detected. To test whether the discriminant power could be increased by adding the genotypes of rs2235040, the second strongest associated SNP, we included this polymorphism in the analysis. While both SNPs contributed significantly to the discriminant power (rs2235015: Wilks lambda=0.792, $p=1.0\times10^{-5}$ and rs2235040: Wilks lambda=0.875, $p=0.0008$), the addition of the second genotype did not increase the number of correctly classified patients in the citalopram/paroxetine/venlafaxine group. This would indicate that genotyping rs2235015 is sufficient to predict remission status with a certainty of over 75% in patients receiving ABCB1 substrates. FIG. 3 shows a distribution of rs2235015 genotype among remitters and non-remitters for patients treated with mirtazapine vs. citalopram/paroxetine/venlafaxine.

2.5 rs2235015 genotype is not associated with differences in drug plasma levels

Figure 4:
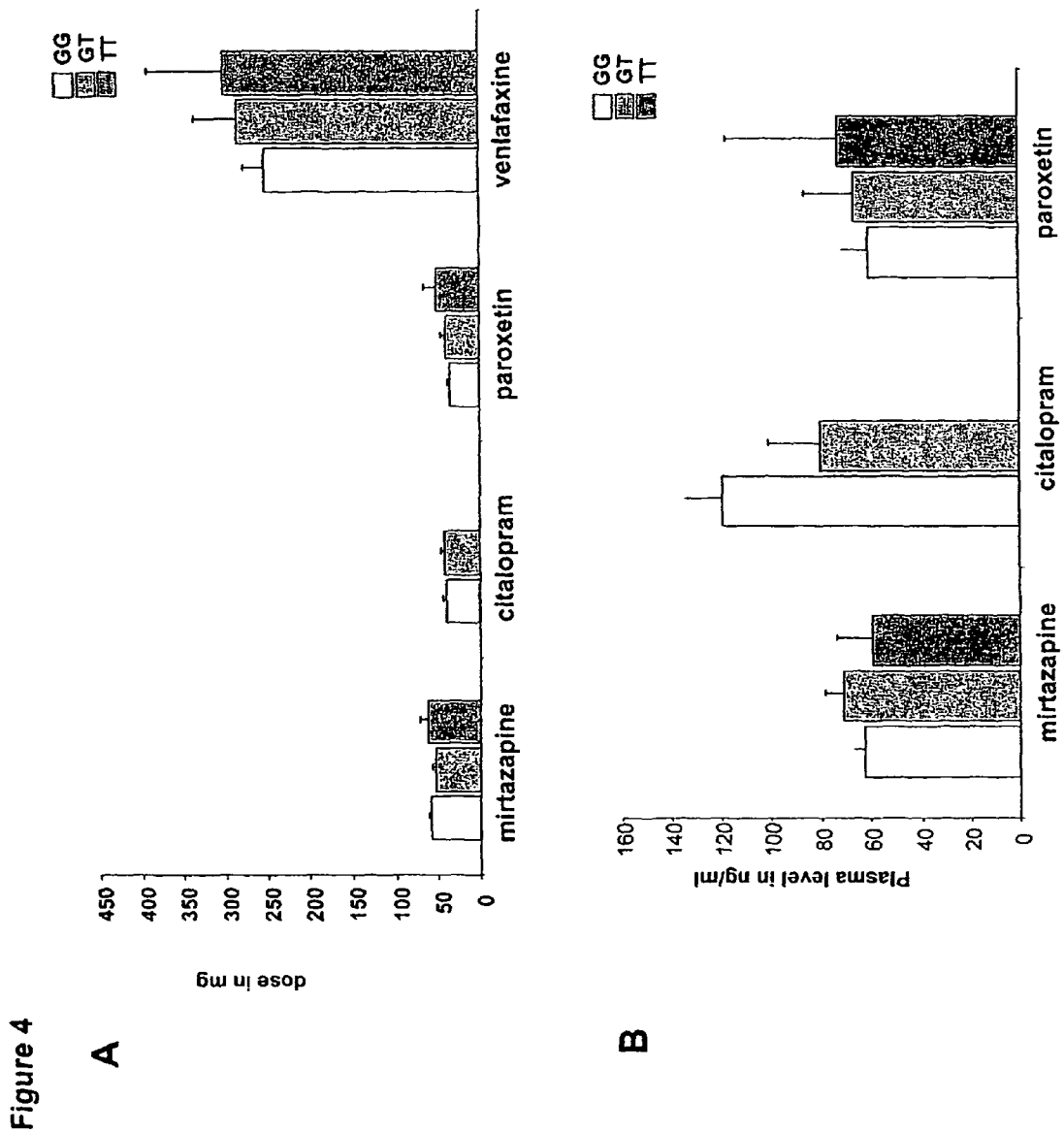

SNPs in ABCB1 have been reported to influence intestinal uptake and thus plasma levels of drugs[15,16]. Differences in plasma levels may also lead to differences in the tolerance of the drug and thus potentially to differences in drug dosing. To exclude that the effect we are seeing is solely based on differences in intestinal uptake, we compared plasma levels and administered doses of citalopram (N=35), paroxetine (N=29), venlafaxine (N=22) and mirtazapine (N=65) according to the genotype of rs2235015. During the course of the study, routine evaluation of plasma venlafaxine levels was only available after half of the patients were recruited, so that for this drug only plasma levels for GG homozygotes were measured. No significant, genotype-dependent difference could be found for the mean plasma levels and administered dose of all four antidepressants over the first six weeks of treatment (see FIGS. 4A and 4B). The possibility that the association of remission status with rs2235015 genotype is related to differences in plasma levels can thus be rejected, supporting the hypothesis that genotype-related differences in treatment response are linked to differences in intracerebral drug concentrations. In addition, we did not observe any differences in rs2235015 genotype distribution among the four drugs, indicating that the genotype did not influence the choice of the administered antidepressant.

3. DISCUSSION

This study shows for the first time that antidepressant-induced remission of depressive symptoms can be predicted by a SNP, particularly by rs2235015 in the ABCB1 gene. This association between clinical course and the ABCB1 polymorphism is found in depressed patients treated with drugs that are a substrate of the ABCB1 encoded p-glycoprotein. To identify whether or not the antidepressants administered to patients are substrates of the p-glycoprotein, mouse mutants were studied lacking the mouse homologues of the ABCB1 gene. These findings underscore the need to classify antidepressants according to their property as p-glycoprotein substrate.

So far, it has not been possible to predict the affinity of a substrate to p-glycoprotein from the chemical structure, from hydrophobicity, lipophilicity or charge. Structural characteristics that allow to explain why venlafaxine, citalopram and paroxetine are substrates, but mirtazapine is not, have not been identified. Therefore, an animal model, in this case mouse mutants lacking ABCB1 homologues are helpful in assessing whether a given antidepressant is a substrate of p-glycoprotein. These results suggest a similar substrate-specificity between mouse and man, supporting that mice with abcb1a and abcb1b null-mutations are appropriate models for human ABCB1 loss of function.

Numerous papers describe polymorphisms in this ABCB1[17-24] and over 230 SNPs are listed in public SNP databases for ABCB1. The most studied polymorphism is a silent SNP, rs1045642 in exon 26 (27 according to the human reference sequence; UCSC version hg15), often referred to as C3435T[14,16] found an association between this C3435T polymorphism and drug-resistant epilepsy, suggesting possible effects of this polymorphism on intracerebral concentrations of antiepileptic drugs. In this study, however, no distinction was made according to the p-glycoprotein substrate status of the used anticonvulsants. Only one study investigated ABCB1 polymorphisms, more specifically C3435T, in relation to antidepressant-induced clinical effects[25]. In this study, patients were treated with nortriptyline, substrate of p-glycoprotein or fluoxetine, which is not substrate of p-glycoprotein[26,27]. No significant association was found between the C3435T genotype and antidepressant response to either drug, which is in agreement with the lack of association with remission status at 6 weeks that we observe with this same polymorphism.

In conclusion, the herein reported finding that genotyping specific polymophisms, such as rs2235015 would allow to predict clinical response to a distinct class of antidepressants is a further step towards differential therapy according to individual genetic background. Substrates of p-glycoprotein could be drug of choice in patients with the GT or TT genotypes of rs2235015 (see FIG. 3). Furthermore, patients with the GG genotype, presumably associated with insufficient intracerebral concentrations of antidepressants substrates of p-glycoprotein may benefit from co-medication with a drug that by blocking the ABCB1-transporter enhances intracerebral antidepressant concentrations. Beside the benefit for the individual patient receiving drugs customised to his or her genotype, the prediction of response by genotype poses important questions for the recruitment and enrolment of trial participants. Once a difference in substrate specificity for p-glycoprotein is established for two comparative drugs the current findings call for appropriate stratification of clinical study samples, to avoid sampling biases. Such a bias can have serious consequences as the drug-response profiles will not reflect those of the general population.

REFERENCES

1. Thase, M. E. Overview of antidepressant therapy. *Manag. Care* 10, 6-9, Discussion 18-22 (2001).
2. Cordon-Cardo, C., O'Brien, J. P., Casals, D., Rittman-Grauer, L., Biedler, J. L., Melamed, M. R. & Bertino, J. R. Multidrug-resistance gene (P-glycoprotein) is expressed by endothelial cells at blood-brain barrier sites. *Proc. Natl. Acad. Sci. USA* 86, 695-698 (1989).
3. Thiebaut, F., Tsuruo, T., Hamada, H., Gottesman, M. M., Pastan, I. & Willingham, M. C. Cellular localization of the multidrug-resistance gene product P-glycoprotein in normal human tissues. *Proc. Natl. Acad. Sci. USA* 84, 7735-7738 (1987).
4. Ambudkar, S. V., Dey, S., Hrycyna, C. A., Ramachandra, M., Pastan, I. & Gottesman, M. M. Biochemical, cellular, and pharmacological aspects of the multidrug transporter. *Annu. Rev. Pharmacol. Toxicol.* 39, 361-398 (1999).
5. Callen, D. F., Baker, E., Simmers, R. N., Seshadri, R. & Roninson, I. B. Localization of the human multiple drug resistance gene, MDR1, to 7q21.1. *Hum. Genet.* 77, 142-144 (1987).
6. Chin, J. E., Soffir, R., Noonan, K. E., Choi, K. & Roninson, I. B. Structure and expression of the human MDR (P-glycoprotein) gene family. *Mol. Cell Biol* 9, 3808-3820 (1989).
7. Schinkel, A. H., Wagenaar, E., Mol, C. A. & van Deemter, L. P-glycoprotein in the blood-brain barrier of mice influences the brain penetration and pharmacological activity of many drugs. *J. Clin. Invest.* 97, 2517-2524 (1996).
8. Uhr, M., Holsboer, F. & Müller, M. B. Penetration of endogenous steroid hormones corticosterone, cortisol, aldosterone and progesterone into the brain is enhanced in mice deficient for both mdr1a and mdr1b P-glycoproteins. *J. Neuroendocrinol.* 14, 753-759 (2002).
9. Devault, A. & Gros, P. Two members of the mouse mdr gene family confer multidrug resistance with overlapping but distinct drug specificities. *Mol. Cell Biol.* 10, 1652-1663 (1990).
10. Meijer, O. C., de Lange, E. C., Breimer, D. D., de Boer, A. G., Workel, J. O. & de Kloet, E. R. Penetration of dexamethasone into brain glucocorticoid targets is enhanced in mdr1A P-glycoprotein knockout mice. *Endocrinology* 139, 1789-1793 (1998).
11. van de Vrie, W., Marquet, R. L., Stoter, G., de Bruijn, E. A. & Eggermont, A. M. In vivo model systems in P-glycoprotein-mediated multidrug resistance. *Crit. Rev. Clin. Lab. Sci.* 35, 1-57 (1998).
12. Uhr, M., Grauer, M. T. & Holsboer, F. Differential enhancement of antidepressant penetration into the brain in mice with abcb1ab (mdr1ab) P-glycoprotein gene disruption. *Biol. Psychiatry* 54, 840-846 (2003).
13. Kroetz, D. L., Pauli-Magnus, C., Hodges, L. M., Huang, C. C., Kawamoto, M., Johns, S. J., Stryke, D., Ferrin, T. E., DeYoung, J., Taylor, T., Carlson, E. J., Herskowitz, I., Giacomini, K. M. & Clark, A. G. Sequence diversity and haplotype structure in the human ABCB1 (MDR1, multidrug resistance transporter) gene. *Pharmacogenetics* 13, 481-494 (2003).
14. Siddiqui, A., Kerb, R., Weale, M. E., Brinkmann, U., Smith, A., Goldstein, D. B., Wood, N. W. & Sisodiya, S. M. Association of multidrug resistance in epilepsy with a polymorphism in the drug-transporter gene ABCB1. *N. Engl. J. Med.* 348, 1442-1448 (2003).
15. Sakaeda, T., Nakamura, T. & Okumura K. Pharmacogenetics of MDR1 and its impact on the pharmacokinetics and pharmacodynamics of drugs. *Pharmacogenomics* 4, 397-410 (2003).
16. Brinkmann, U. Functional polymorphisms of the human multidrug resistance (MDR1) gene: correlation with P glycoprotein expression and activity in vivo. *Novartis Found. Symp.* 243, 207-212. (2002).
17. Kioka, N., Tsubota, J., Kakehi, Y., Komano, T., Gottesman, M. M., Pastan, I. & Ueda, K. P-glycoprotein gene (MDR1) cDNA from human adrenal: normal P-glycoprotein carries Gly185 with an altered pattern of multidrug resistance. *Biochem. Biophys. Res Commun.* 162, 224-231 (1989).
18. Stein, U., Walther, W. & Wunderlich, V. Point mutations in the mdr1 promoter of human osteosarcomas are associated with in vitro responsiveness to multidrug resistance relevant drugs. *Eur. J. Cancer* 30A, 1541-1545 (1994).

19. Mickley, L. A., Lee, J. S., Weng, Z., Zhan, Z., Alvarez, M., Wilson, Bates, S. E. & Fojo, T. Genetic polymorphism in MDR-1: a tool for examining allelic expression in normal cells, unselected and drug-selected cell lines, and human tumors. *Blood* 91, 1749-1756 (1998).
20. Hoffmeyer, S., Burk, O., von Richter, O., Arnold, H. P., Brockmoller, J., Johne, A., Cascorbi, I., Gerloff, T., Roots, I., Eichelbaum, M. & Brinkmann, U. Functional polymorphisms of the human multidrug-resistance gene: multiple sequence variations and correlation of one allele with P-glycoprotein expression and activity in vivo. *Proc. Natl. Acad. Sci. USA* 97, 3473-3478 (2000).
21. Ito, S., Ieiri, I., Tanabe, M., Suzuki, A., Higuchi, S. & Otsubo, K. Polymorphism of the ABC transporter genes, MDR1, MRP1 and MRP2/cMOAT, in healthy Japanese subjects. *Pharmacogenetics* 11, 175-184 (2001).
22. Cascorbi, I., Gerloff, T., Johne, A., Meisel, C., Hoffmeyer, S., Schwab, M., Schaeffeler, E., Eichelbaum, M., Brinkmann, U. & Roots, I. Frequency of single nucleotide polymorphisms in the P-glycoprotein drug transporter MDR1 gene in white subjects. *Clin. Pharmacol. Ther.* 69, 169-174 (2001).
23. Tanabe, M., Ieiri, I., Nagata, N., Inoue, K., Ito, S., Kanamori, Y., Takahashi, M., Kurata, Y., Kigawa, J., Higuchi, S., Terakawa, N. & Otsubo, K. Expression of P-glycoprotein in human placenta: relation to genetic polymorphism of the multidrug resistance (MDR)-1 gene. *J. Pharmacol. Exp. Ther.* 297, 1137-1143 (2001).
24. Kim, R. B., Leake, B. F., Choo, E. F., Dresser, G. K., Kubba, S. V., Schwarz, U. I., Taylor, A., Xie, H. G., McKinsey, J., Zhou, S., Lan, L. B., Schuetz, J. D., Schuetz, E. G. & Wilkinson, G. R. Identification of functionally variant MDR1 alleles among European Americans and African Americans. *Clin. Pharmacol. Ther.* 70, 189-199 (2001).
25. Roberts, R. L., Joyce, P. R., Mulder, R. T., Begg, E. & Kennedy, M. A. A common P-glycoprotein polymorphism is associated with nortriptyline-induced postural hypotension in patients treated for major depression. *Pharmacogenomics J.* 2, 191-196 (2002).
26. Uhr, M. & Grauer, M. T. abcb1ab P-glycoprotein is involved in the uptake of citalopram and trimipramine into the brain of mice. *J. Psychiatric Res.* 37, 179-185 (2003).
27. Uhr, M., Steckler, T., Yassouridis, A. & Holsboer, F. Penetration of amitriptyline, but not of fluoxetine, into brain is enhanced in mice with blood-brain-barrier deficiency due to Mdr1a P-glycoprotein gene disruption. *Neuropsychopharmacology* 22, 380-387 (2000).
28. Schinkel, A. H., Mayer, U., Wagenaar, E., Mol, C. A., van Deemter, L., Smit, J. J., van der Valk, M. A., Voordouw, A. C., Spits, H., van Tellingen, O., Zijlmans, J. M., Fibbe, W. E. & Borst, P. Normal viability and altered pharmacokinetics in mice lacking mdr1-type (drug-transporting) P-glycoproteins. *Proc. Natl. Acad. Sci. USA* 94, 4028-4033 (1997).
29. Uhr, M., Grauer, M. T. & Holsboer, F., Differentiqal Enhancement of Antidepressant Penetration into the Brain of Mice with abcb1ab (mdr1ab) P-Glycoprotein Disruption, Biol. Psych. 34, 840-846 (2003).
30. De Luca, V., Mundo, E., Trakalo, J., Wong, G. W. M. & Kennedy, J. L. Investigation of polymorphism in the MDR1 gene and antidepressant-induced mania. Pharmacogenomics J. 3, 297-299 (2003).
31. Marzolini, C., Pans, E., Buchin, T. & Kim, R. B. Polymorphisms in human MDR1 (P-glycoprotein): Recent advances and clinical relevance. Clin. Pharmacol. Ther. 75, 13-33 (2004).

The invention claimed is:

1. A method for determining the prognosis of a clinical response in a human patient to a central nervous system (CNS)-active medicament which is a substrate of the ABCB1 protein comprising the step of performing a genotyping analysis of a biological sample from the patient to determine the presence of at least one polymorphism in the ABCB1 gene of said patient wherein said polymorphism is selected from the group consisting of rs 2235015, rs 2235040, is 2235067, rs 2032583, is 17064, rs2032588, is 1055302, and combinations thereof as well as polymorphisms that are in linkage disequilibrium with said at least one polymorphism, where the presence of said polymorphism is associated with remission to said CNS-active medicament which is a substrate of the ABCB1 protein, and determining a prognosis for said patient based on said genotyping analysis.

2. The method of claim 1, wherein the polymorphism is rs 2235015 or rs 2235040.

3. The method of claim 2 wherein the polymorphism is rs 2235015.

4. The method of claim 1, wherein the genotyping analysis comprises the use of polymorphism-specific primers and/or probes.

5. The method of claim 4 wherein the genotyping analysis comprises a primer extension reaction.

6. The method of claim 4, wherein the primers and/or probes comprise at least one sequence selected from the group consisting of SEQ ID NO: 8 to SEQ ID NO: 32.

7. The method of claim 4 wherein the genotyping analysis comprises a microarray analysis.

8. The method of claim 4 wherein the genotyping analysis comprises a mass-spectrometric analysis.

9. The method of claim 1, wherein the medicament is selected from the group consisting of antidepressants, anxiolytics, hypnotics, cognitive enhancers, antipsychotics, neuroprotective agents, antiemetics, antiepileptics, antibiotics, anticancer agents, antimycotics, antiparkinson agents, antiviral agents, glucocorticoids, immunosuppressants, statins, neuroleptics, and opioids.

10. The method of claim 9 wherein the medicament is an antidepressant.

11. The method of claim 10 wherein the antidepressant is citalopram, venlafaxine and/or paroxetine.

12. A method of obtaining a clinical response in a human patient in need thereof comprising determining the prognosis of a clinical response in said patient to a central nervous system-active medicament which is a substrate of the ABCB1 protein by performing a genotyping analysis of a biological sample from the patient to determine the presence of at least one polymorphism in the ABCB1 gene of said patient, wherein said polymorphism is selected from the group consisting of rs 2235015, rs 2235040, is 2235067, rs 2032583, is 17064, rs2032588, is 1055302, and combinations thereof as well as polymorphisms that are in linkage disequilibrium with said at least one polymorphism, where the presence of said polymorphism is associated with remission to said CNS-active medicament which is a substrate of the ABCB1 protein, and thereafter administering said medicament to said patient according to the results of the determination of said polymorphism.

13. The method of claim 12 wherein, if the determination of said polymorphism gives a favorable prognosis for a clinical response, the medicament is administered in a standard dose.

14. The method of claim 12 wherein, if the determination of said polymorphism gives an unfavorable prognosis for a clinical response, the medicament is administered in a dose which is higher than the standard dose.

15. The method of claim 12 wherein, if the determination of said polymorphism gives an unfavorable prognosis for a clinical response, the medicament is administered in combination with a further medicament which is an inhibitor of the ABCB1 protein.

16. The method of claim 12 wherein, if the determination of said polymorphism gives an unfavorable prognosis for a clinical response, the medicament is administered in a formulation which shows an increased permeation through the blood-brain barrier.

* * * * *

SEQUENCE LISTING

```
<160> NUMBER OF SEQ ID NOS: 32

<210> SEQ ID NO 1
<211> LENGTH: 31
<212> TYPE: DNA
<213> ORGANISM: Homo sapiens
<220> FEATURE:
<221> NAME/KEY: misc_feature
<222> LOCATION: (6)..(9)
<223> OTHER INFORMATION: n is a, c, g, or t

<400> SEQUENCE: 1
aacacnnnna gaattwtgaa gaggtatctg t                              31

<210> SEQ ID NO 2
<211> LENGTH: 31
<212> TYPE: DNA
<213> ORGANISM: Homo sapiens

<400> SEQUENCE: 2
ctcctttcta ctggtrtttg tcttaattgg c                              31

<210> SEQ ID NO 3
<211> LENGTH: 31
<212> TYPE: DNA
<213> ORGANISM: Homo sapiens

<400> SEQUENCE: 3
aaagtacaag accctraact aaggcaggga c                              31
```

```
<210> SEQ ID NO 4
<211> LENGTH: 31
<212> TYPE: DNA
<213> ORGANISM: Homo sapiens

<400> SEQUENCE: 4
tagagtaaag tattcyaatc agtgttattt t                               31

<210> SEQ ID NO 5
<211> LENGTH: 31
<212> TYPE: DNA
<213> ORGANISM: Homo sapiens
<220> FEATURE:
<221> NAME/KEY: misc_feature
<222> LOCATION: (6)..(9)
<223> OTHER INFORMATION: n is a, c, g, or t

<400> SEQUENCE: 5
aacacnnnna gaattwtgaa gaggtatctg t                               31

<210> SEQ ID NO 6
<211> LENGTH: 31
<212> TYPE: DNA
<213> ORGANISM: Homo sapiens

<400> SEQUENCE: 6
gcggtgatca gcagtyacat tgcacatctt t                               31

<210> SEQ ID NO 7
<211> LENGTH: 31
<212> TYPE: DNA
<213> ORGANISM: Homo sapiens

<400> SEQUENCE: 7
cccaaaacac agatcratat aagattttag g                               31

<210> SEQ ID NO 8
<211> LENGTH: 30
<212> TYPE: DNA
<213> ORGANISM: Homo sapiens

<400> SEQUENCE: 8
acgttggatg cacctagacc accacaaaac                                 30

<210> SEQ ID NO 9
<211> LENGTH: 30
<212> TYPE: DNA
<213> ORGANISM: Homo sapiens

<400> SEQUENCE: 9
acgttggatg aaaactgagt cagttcgacc                                 30

<210> SEQ ID NO 10
<211> LENGTH: 30
<212> TYPE: DNA
<213> ORGANISM: Homo sapiens

<400> SEQUENCE: 10
acgttggatg actggagcat tgactaccag                                 30

<210> SEQ ID NO 11
<211> LENGTH: 30
<212> TYPE: DNA
<213> ORGANISM: Homo sapiens
```

```
<400> SEQUENCE: 11
acgttggatg ttagtttcat gctggggtcc                              30

<210> SEQ ID NO 12
<211> LENGTH: 30
<212> TYPE: DNA
<213> ORGANISM: Homo sapiens

<400> SEQUENCE: 12
acgttggatg agtggagaaa gtgctcgaag                              30

<210> SEQ ID NO 13
<211> LENGTH: 30
<212> TYPE: DNA
<213> ORGANISM: Homo sapiens

<400> SEQUENCE: 13
acgttggatg ttctacctca gagatgtccc                              30

<210> SEQ ID NO 14
<211> LENGTH: 29
<212> TYPE: DNA
<213> ORGANISM: Homo sapiens

<400> SEQUENCE: 14
acgttggatg ctgggaaggt gagtcaaac                               29

<210> SEQ ID NO 15
<211> LENGTH: 30
<212> TYPE: DNA
<213> ORGANISM: Homo sapiens

<400> SEQUENCE: 15
acgttggatg gcatagtaag cagtagggag                              30

<210> SEQ ID NO 16
<211> LENGTH: 30
<212> TYPE: DNA
<213> ORGANISM: Homo sapiens

<400> SEQUENCE: 16
acgttggatg gactctgaac ttgactgagg                              30

<210> SEQ ID NO 17
<211> LENGTH: 30
<212> TYPE: DNA
<213> ORGANISM: Homo sapiens

<400> SEQUENCE: 17
acgttggatg gtgaactctg actgtatgag                              30

<210> SEQ ID NO 18
<211> LENGTH: 30
<212> TYPE: DNA
<213> ORGANISM: Homo sapiens

<400> SEQUENCE: 18
acgttggatg tgatgcagag gctctatgac                              30

<210> SEQ ID NO 19
<211> LENGTH: 30
<212> TYPE: DNA
<213> ORGANISM: Homo sapiens
```

```
<400> SEQUENCE: 19
acgttggatg ggcaacatca gaaagatgtg                                              30

<210> SEQ ID NO 20
<211> LENGTH: 30
<212> TYPE: DNA
<213> ORGANISM: Homo sapiens

<400> SEQUENCE: 20
acgttggatg tccacattaa ggtggctctc                                              30

<210> SEQ ID NO 21
<211> LENGTH: 30
<212> TYPE: DNA
<213> ORGANISM: Homo sapiens

<400> SEQUENCE: 21
acgttggatg tcataattgt gcctcacccc                                              30

<210> SEQ ID NO 22
<211> LENGTH: 20
<212> TYPE: DNA
<213> ORGANISM: Homo sapiens

<400> SEQUENCE: 22
accaccacaa aacaaacata                                                         20

<210> SEQ ID NO 23
<211> LENGTH: 18
<212> TYPE: DNA
<213> ORGANISM: Homo sapiens

<400> SEQUENCE: 23
tgcctccttt ctactggt                                                           18

<210> SEQ ID NO 24
<211> LENGTH: 19
<212> TYPE: DNA
<213> ORGANISM: Homo sapiens

<400> SEQUENCE: 24
agagaaagta caagaccct                                                          19

<210> SEQ ID NO 25
<211> LENGTH: 22
<212> TYPE: DNA
<213> ORGANISM: Homo sapiens

<400> SEQUENCE: 25
aattaagtag agtaaagtat tc                                                      22

<210> SEQ ID NO 26
<211> LENGTH: 23
<212> TYPE: DNA
<213> ORGANISM: Homo sapiens

<400> SEQUENCE: 26
aatgttaaac agatacctct tca                                                     23

<210> SEQ ID NO 27
<211> LENGTH: 17
<212> TYPE: DNA
<213> ORGANISM: Homo sapiens
```

```
<400> SEQUENCE: 27
ctgcggtgat cagcagt                                              17

<210> SEQ ID NO 28
<211> LENGTH: 19
<212> TYPE: DNA
<213> ORGANISM: Homo sapiens

<400> SEQUENCE: 28
caaacccaaa acacagatc                                            19

<210> SEQ ID NO 29
<211> LENGTH: 22
<212> TYPE: DNA
<213> ORGANISM: Homo sapiens

<400> SEQUENCE: 29
caattaaaac tgagtcagtt cg                                        22

<210> SEQ ID NO 30
<211> LENGTH: 25
<212> TYPE: DNA
<213> ORGANISM: Homo sapiens

<400> SEQUENCE: 30
ttttaaacat ttctacaact tgatg                                     25

<210> SEQ ID NO 31
<211> LENGTH: 29
<212> TYPE: DNA
<213> ORGANISM: Homo sapiens
<220> FEATURE:
<221> NAME/KEY: misc_feature
<222> LOCATION: (29)..(29)
<223> OTHER INFORMATION: fluorescein label

<400> SEQUENCE: 31
tgtatcattg atatcaccta gaccaccac                                 29

<210> SEQ ID NO 32
<211> LENGTH: 25
<212> TYPE: DNA
<213> ORGANISM: Homo sapiens
<220> FEATURE:
<221> NAME/KEY: misc_feature
<222> LOCATION: (1)..(1)
<223> OTHER INFORMATION: fluorophore label

<400> SEQUENCE: 32
aaacaaacat accatttatg tctct                                     25
```